US012653521B2

(12) United States Patent
Suh et al.

(10) Patent No.: US 12,653,521 B2
(45) Date of Patent: Jun. 16, 2026

(54) ASSISTIVE DEVICE FOR SCALP SUTURING

(71) Applicant: SEOUL NATIONAL UNIVERSITY HOSPITAL, Seoul (KR)

(72) Inventors: Dong Bum Suh, Seongnam-si (KR); Dae Kon Kim, Seongnam-si (KR)

(73) Assignee: SEOUL NATIONAL UNIVERSITY HOSPITAL, Seoul (KR)

( * ) Notice: Subject to any disclaimer, the term of this patent is extended or adjusted under 35 U.S.C. 154(b) by 141 days.

(21) Appl. No.: 18/580,390

(22) PCT Filed: Jul. 19, 2022

(86) PCT No.: PCT/KR2022/010513
§ 371 (c)(1),
(2) Date: Mar. 22, 2024

(87) PCT Pub. No.: WO2023/003314
PCT Pub. Date: Jan. 26, 2023

(65) Prior Publication Data
US 2025/0127505 A1 Apr. 24, 2025

(30) Foreign Application Priority Data

Jul. 19, 2021 (KR) ........................ 10-2021-0093889

(51) Int. Cl.
*A61B 17/04* (2006.01)
(52) U.S. Cl.
CPC .. *A61B 17/0466* (2013.01); *A61B 2017/0488* (2013.01)
(58) Field of Classification Search
CPC .......... A61B 17/0466; A61B 17/00491; A61B 17/08; A61B 17/0487; A61B 2017/0488;
(Continued)

(56) References Cited

U.S. PATENT DOCUMENTS 3,696,823 A * 10/1972 Dannat .................. A45D 24/02
132/122
3,735,765 A * 5/1973 Ichelson ................ A61B 17/08
606/135
(Continued)

FOREIGN PATENT DOCUMENTS

JP 5356542 B2 12/2013
KR 20110093149 A 8/2011
KR 20150115838 A 10/2015

OTHER PUBLICATIONS

PCT Written Opinion of the International Searching Authority for corresponding PCT Application No. PCT/KR2022/010513, dated Nov. 16, 2022, 4 pages.*

(Continued)

*Primary Examiner* — Tan-Uyen T Ho
*Assistant Examiner* — Osama Nemer
(74) *Attorney, Agent, or Firm* — Dority & Manning, PA

(57) ABSTRACT

An assistive device for scalp suturing that allows the hair apposition technique (HAT) procedure to be easily performed even by a single operator. The assistive device for scalp suturing includes: a housing including a frame formed in a circular or polygonal shape having a slot therein and a mounting groove formed on at least some areas of the frame, wherein the slot is positioned at a scalp laceration site; a plurality of knot holes provided on at least some areas of an outer side of the housing; and first and second hair fixers detachably mounted on the mounting groove of the housing and configured to fix hair around the scalp laceration site.

7 Claims, 5 Drawing Sheets

(58) Field of Classification Search
CPC .... A61B 2017/00353; A61B 2017/081; A61B
2017/00424; A61B 2017/0464; A61B
90/14; A45D 24/00
See application file for complete search history.

(56) References Cited

U.S. PATENT DOCUMENTS

| | | | |
|---|---|---|---|
| 3,908,674 A * | 9/1975 | Kessler ................ | A41G 5/0026 |
| | | | 606/187 |
| 2008/0156341 A1 * | 7/2008 | Longoria ................. | A45D 8/20 |
| | | | 132/277 |
| 2019/0223869 A1 | 7/2019 | Krupp et al. | |
| 2020/0205833 A1 * | 7/2020 | Christiansen ........ | A61B 17/085 |
| 2020/0375584 A1 * | 12/2020 | Goetz ................... | A61B 17/10 |

OTHER PUBLICATIONS

PCT International Search Report (with English translation) for
corresponding PCT Application No. PCT/KR2022/010513, mailed
Nov. 16, 2022, 6 pages.

* cited by examiner

[FIG. 1]
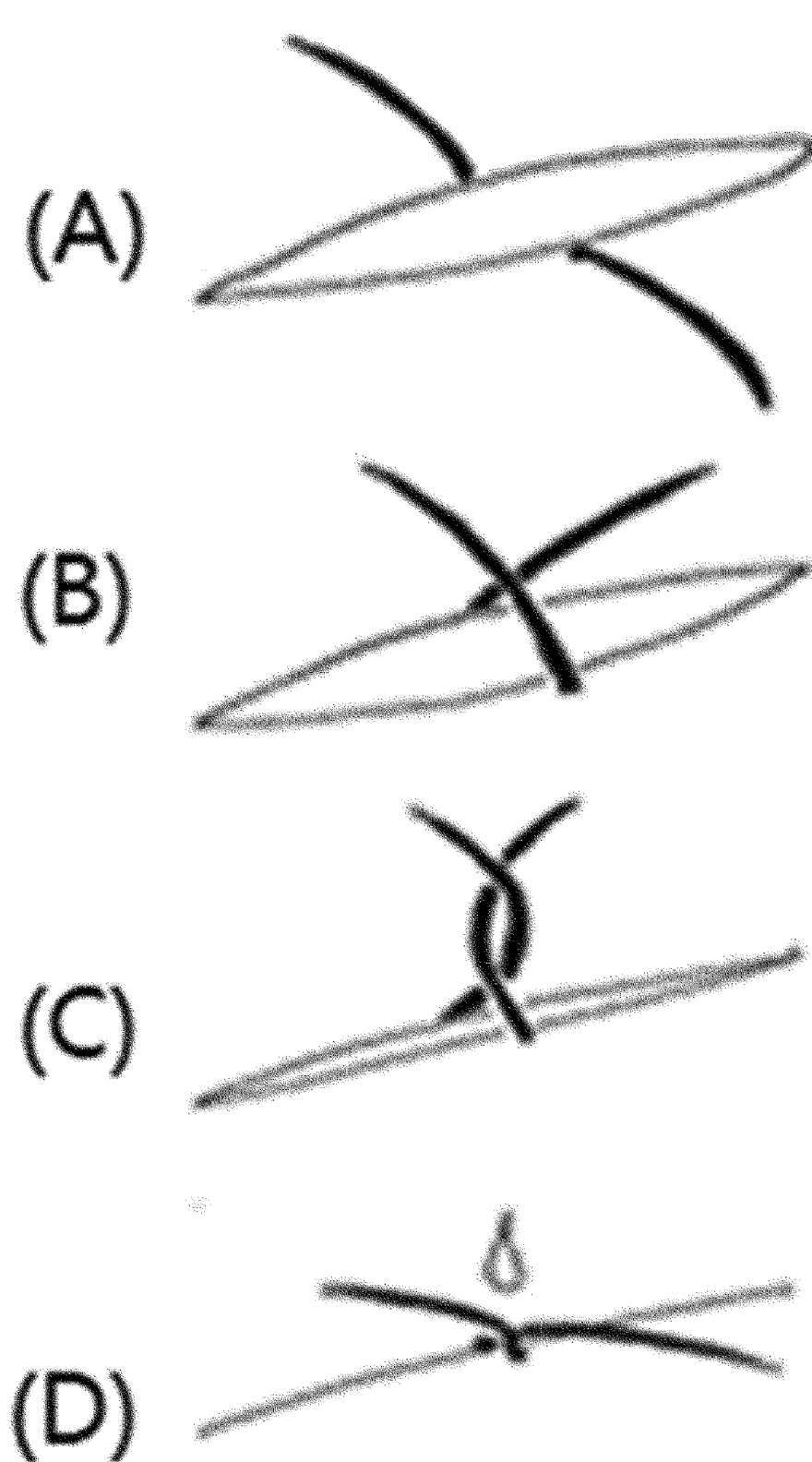

[FIG. 2]
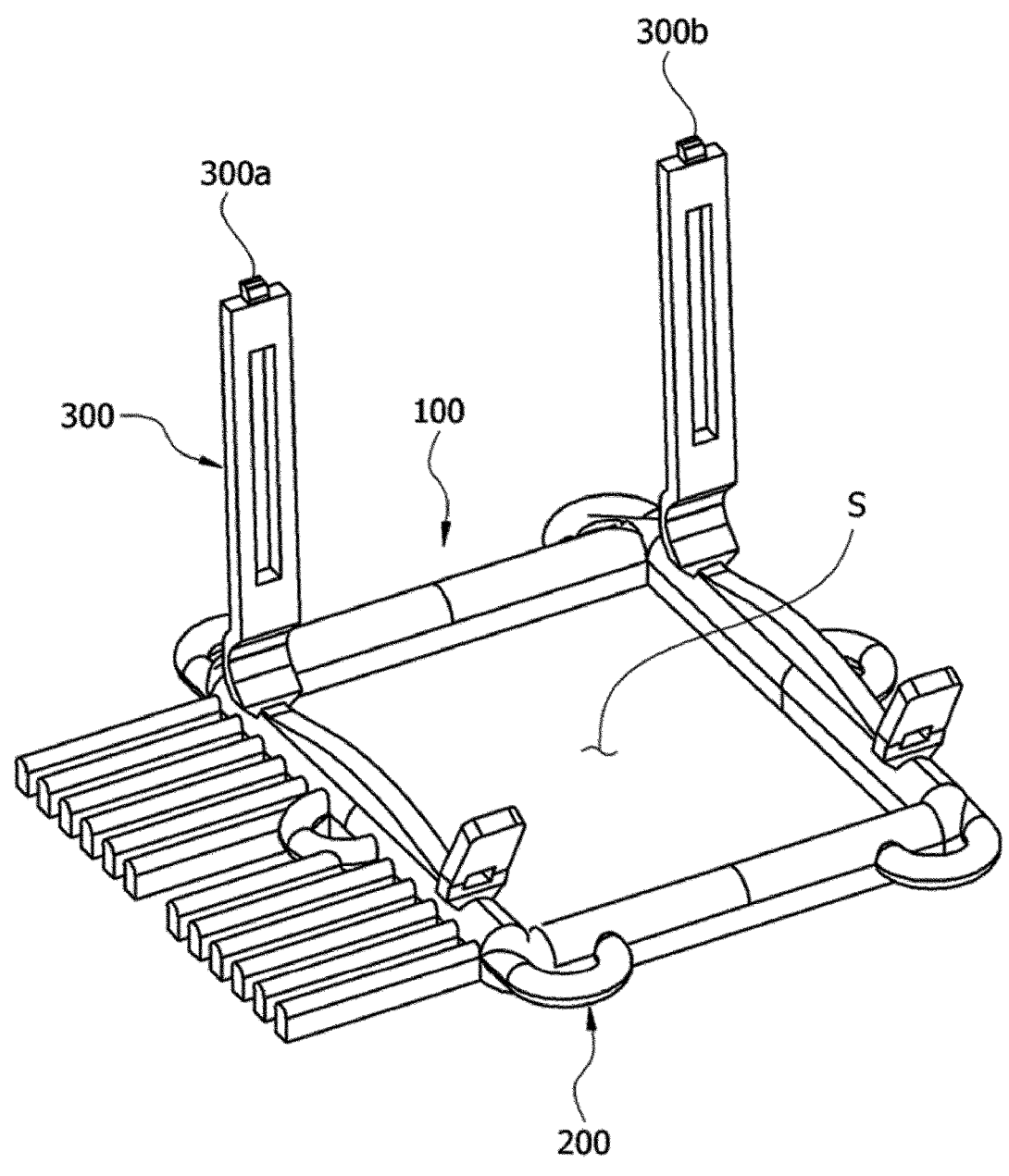

[FIG. 3]
(A)
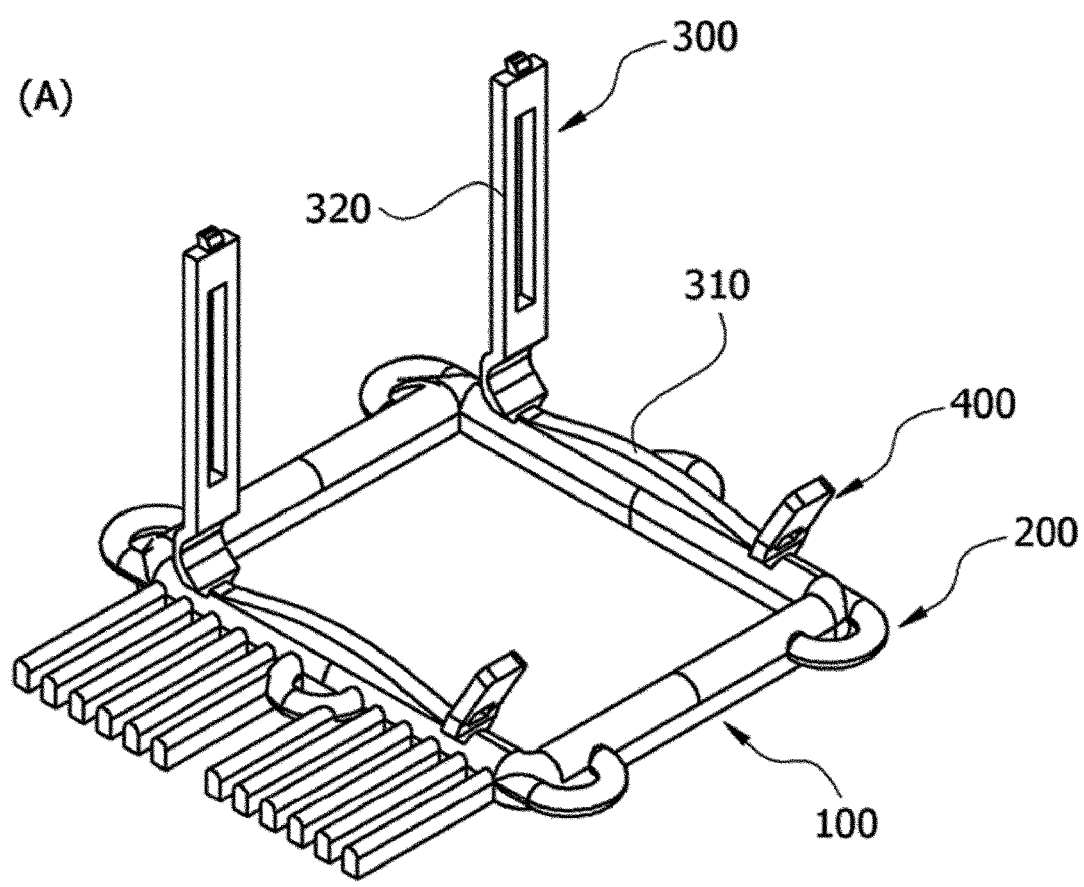
(B)
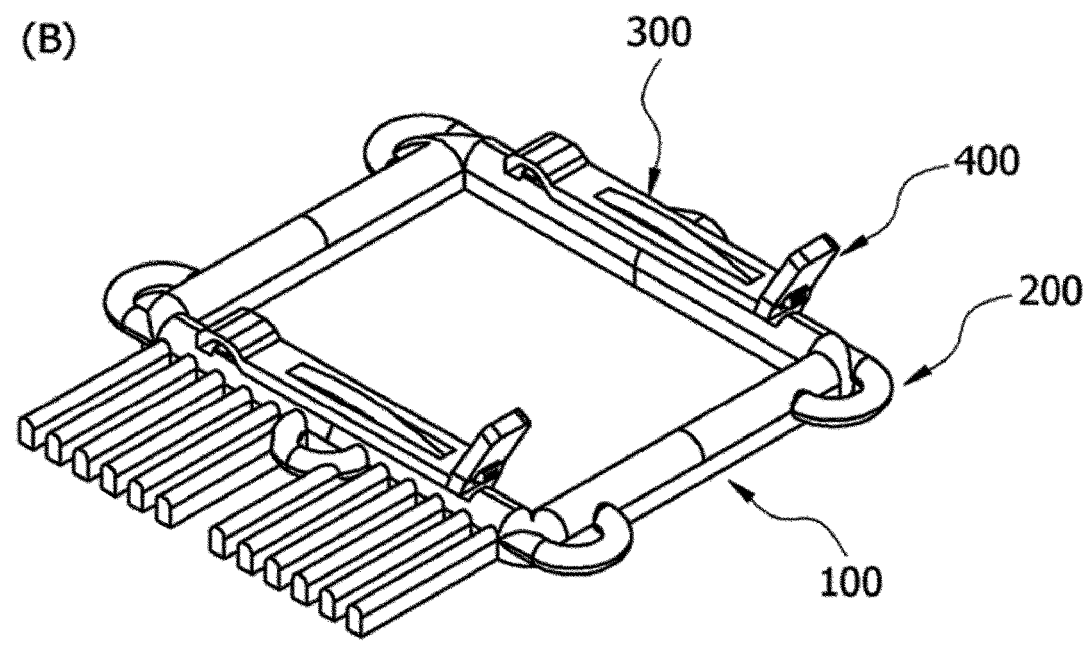

[FIG. 4]
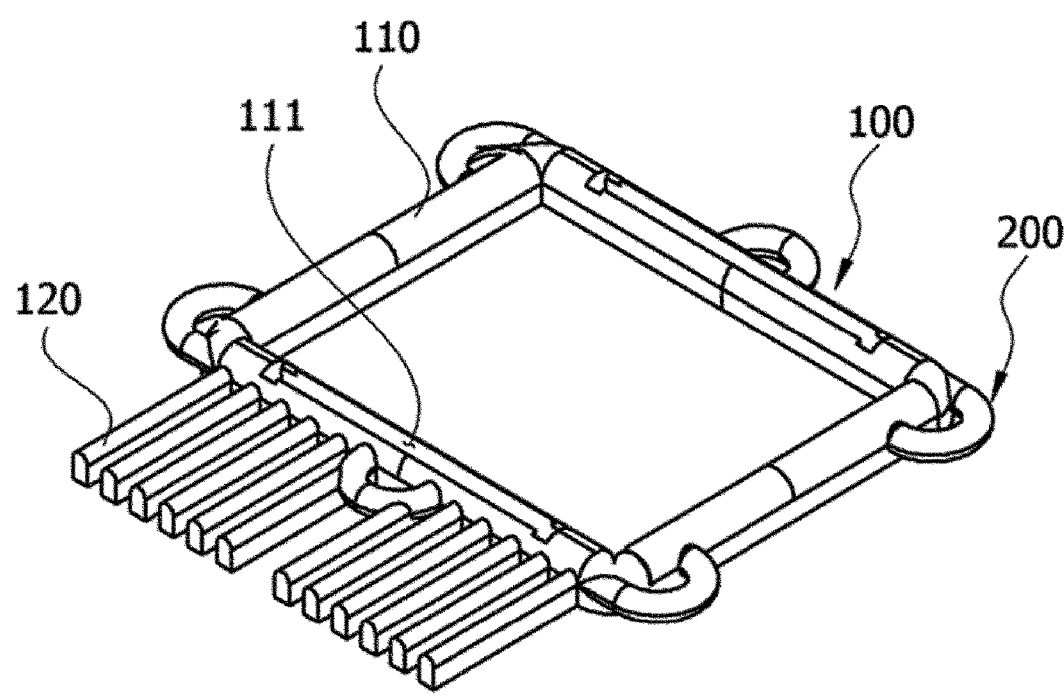

[FIG. 5]
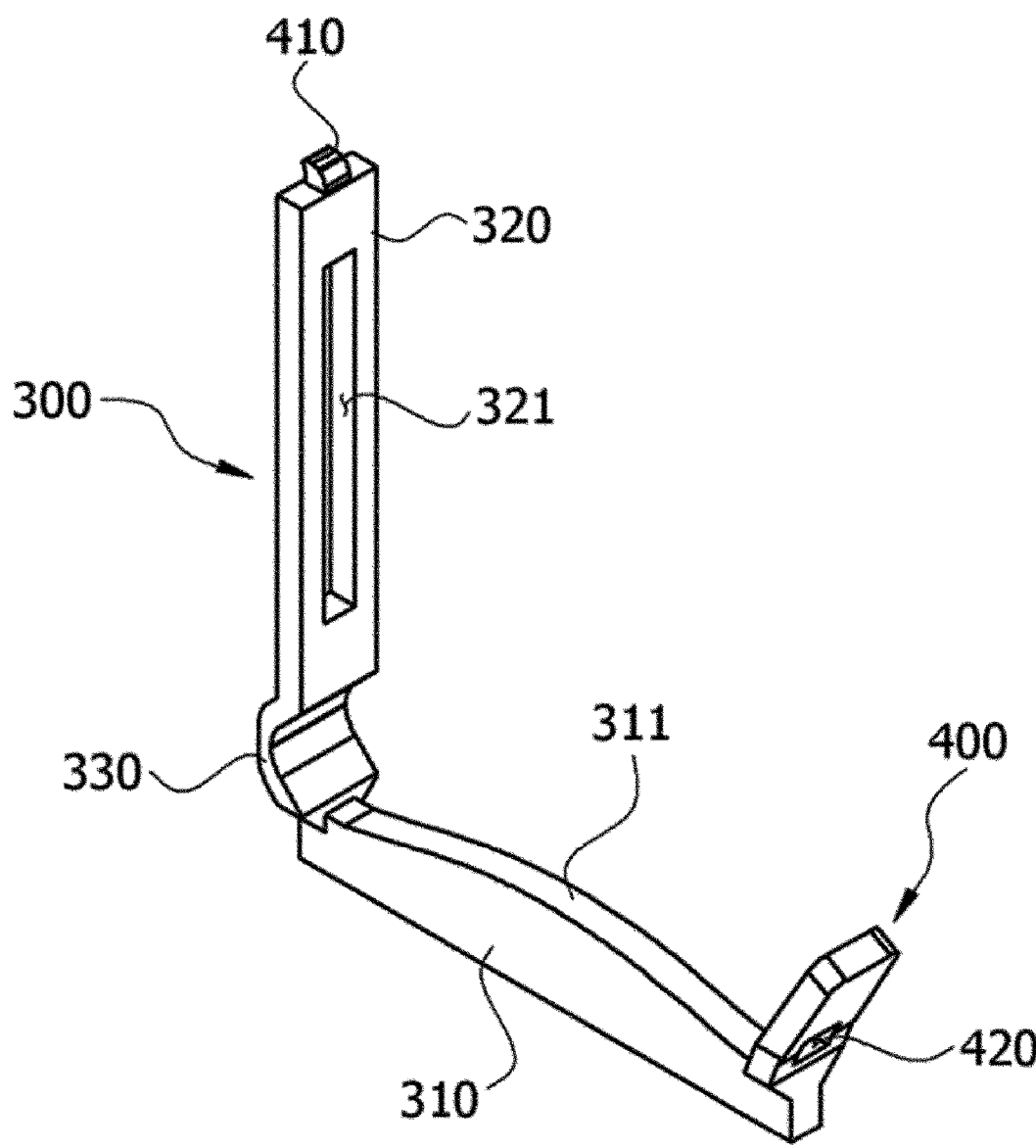

1

ASSISTIVE DEVICE FOR SCALP SUTURING

CROSS-REFERENCE TO RELATED APPLICATIONS

This application is the U.S. National Stage entry of International Application No. PCT/KR2022/010513, filed on Jul. 19, 2022, which, in turn, claims priority to KR Patent Application No. 10-2021-0093889, filed on Jul. 19, 2021, both of which are hereby incorporated herein by reference in their entireties for all purposes.

TECHNICAL FIELD

The present invention relates to an assistive device for scalp suturing.

BACKGROUND ART

Scalp lacerations (or wounds) are a common injury in emergency rooms. According to U.S. statistics, 12 million people visit emergency rooms each year in the U.S., and a large number of them have scalp lacerations. Typical methods of treating scalp lacerations include using sutures or using skin staplers.

However, such treatment methods have problems in that patients are dissatisfied with the treatment because of the need to remove hair at a laceration site, it is difficult to obtain patient's compliance with the treatment due to pain caused during suturing, and especially for infants, it is difficult to perform the treatment unless they are calmed down. Also, there is an inconvenience of having to remove sutures (or staplers) afterwards.

Meanwhile, the hair apposition technique (HAT) method has begun to be used after being reported in 2002 as a new method to suture the scalp.

FIG. 1 illustrates the HAT procedure.

Referring to FIG. 1, the HAT procedure is performed through four main steps A to D. Specifically, after a laceration site is disinfected, hair around the laceration site is parted to both sides based on the laceration site, and several strands of hair at both sides facing each other at the site where suturing is necessary are picked up (step A). The picked-up strands of hair are crossed (step B). Then, the crossed strands of hair are twisted once and pulled to close the laceration site (step C). Lastly, one drop of skin glue is applied onto a knot of the twisted strands of hair to fix the knot (step D).

That is, the HAT procedure is a method in which strands of hair at a laceration site are twisted and a knot of the twisted strands of hair is fixed using skin glue to achieve the same effect as suturing.

However, the HAT procedure requires two or more operators. The main operator needs to use both hands to tie a knot in order to accurately tie a knot of hair, and here, an assistant operator needs to, while parting the hair around the laceration site to both sides based on the laceration site, tidy the hair that is not tied into a knot, and when strands of hair are tied into a knot, drop skin glue onto the knot. However, in most cases, emergency rooms where scalp lacerations are treated lack medical personnel who can get involved in the treatment, and the treatment is often delayed or performed using a skin stapler.

DISCLOSURE

Technical Problem

The present invention is directed to providing an assistive device for closing scalp lacerations that allows the hair apposition technique (HAT) procedure to be easily performed even by a single operator.

Technical Solution

One aspect of the present invention relates to an assistive device for closing scalp lacerations of patients with scalp lacerations and provides an assistive device for scalp suturing that includes: a housing including a frame formed in a circular or polygonal shape having a slot therein and a mounting groove formed on at least some areas of the frame, wherein the slot is positioned at a scalp laceration site; a plurality of knot holes provided on at least some areas of an outer side of the housing; and one or more hair fixers detachably mounted on the mounting groove of the housing and configured to fix hair around the scalp laceration site.

Advantageous Effects

As described above, an assistive device for closing scalp lacerations that relates to at least one embodiment of the present invention allows the hair apposition technique (HAT) procedure to be easily performed even by a single operator.

DESCRIPTION OF DRAWINGS

FIG. 1 is a view illustrating the hair apposition technique (HAT) procedure.

FIG. 2 is a view illustrating an assistive device for closing scalp lacerations according to one embodiment of the present invention.

FIG. 3 is a view illustrating opening and closing operations of hair fixers in the assistive device for closing scalp lacerations that is illustrated in FIG. 2.

FIG. 4 is a detailed view separately illustrating a housing in the assistive device for closing scalp lacerations that is illustrated in FIG. 2.

FIG. 5 is a detailed view separately illustrating a hair fixer in the assistive device for closing scalp lacerations that is illustrated in FIG. 2.

MODES OF THE INVENTION

Hereinafter, various embodiments of the present invention will be described in detail with reference to the accompanying drawings. However, the present invention is not limited or restricted by the embodiments. Also, in various embodiments of the present invention, scales or proportions in each drawing are only illustrative, and components of the present invention illustrated in the drawings according to embodiments may be designed to have different shapes, forms, dimensions, or sizes.

The present invention relates to an assistive device for closing scalp lacerations of patients with scalp lacerations. Specifically, the assistive device for closing scalp lacerations may be a device used in the hair apposition technique (HAT) procedure.

FIG. 2 is a view illustrating an assistive device for closing scalp lacerations according to one embodiment of the present invention, FIG. 3 is a view illustrating opening and closing operations of hair fixers 300 in the assistive device for closing scalp lacerations that is illustrated in FIG. 2, FIG. 4 is a detailed view separately illustrating a housing 100 in the assistive device for closing scalp lacerations that is illustrated in FIG. 2, and FIG. 5 is a detailed view separately illustrating the hair fixer 300 in the assistive device for closing scalp lacerations that is illustrated in FIG. 2.

Referring to the drawings, the assistive device for closing scalp lacerations according to the present invention includes a housing 100, a plurality of knot holes 200, and one or more hair fixers 300.

The housing 100 includes a frame 110 formed in a circular or polygonal shape having a slot S therein and a mounting groove 111 formed on at least some areas of the frame, wherein the slot S is positioned at a scalp laceration site. In a state in which the slot S is placed on the scalp laceration site, an operator may perform the HAT procedure to close the scalp laceration site. The frame 110 may have a circular structure in which a single frame is continuously connected or a polygonal structure in which a plurality of frames are connected. The housing 100 may be manufactured by 3D printing, but the housing 100 is not limited thereto and may be manufactured using a mold to be suitable for mass production. Also, the frame 110 has one surface that comes in contact or close contact with the scalp during the HAT procedure and the other surface disposed in the opposite direction, and the mounting groove 111 may be provided as at least two or more mounting grooves 111 formed to be symmetrical to each other on at least some areas of the other surface of the frame.

The plurality of knot holes 200 are provided on at least some areas of an outer side of the housing 100. The plurality of knot holes 200 may be formed to be symmetrical to each other on an outer side surface of the frame that is in the opposite direction to an inner side surface of the frame facing the slot. For example, in a case where the frame 110 has a quadrangular shape, each knot hole 200 may be provided on one of the four corner portions. The knot hole 200 is a portion for coupling with a separate knotting member. For example, in a state in which the slot S is placed on the scalp laceration site, one portion of the knotting member may be fixed to the chin or ear of the patient, and the other portion of the knotting member may be fixed to the knot hole 200 to allow the housing 100 to be fixed to the scalp of the patient. For example, the knotting member may be a hook-and-loop fastener, an elastic band, or the like, but is not particularly limited thereto.

The one or more hair fixers 300 are detachably mounted on the mounting grooves 111 of the housing 100 and fix the hair around the scalp laceration site. The hair fixers 300 tidy and fix the hair around the scalp laceration site to prevent the hair from interfering with the HAT procedure. The hair fixers 300 may be provided as a plurality of hair fixers 300 that correspond to the number of the mounting grooves 111. For example, in a case where the number of the mounting grooves 111 is two, the number of the hair fixers 300 may also be two. As another example, the hair fixer 300 may be integrally connected to the mounting groove 111 so as not to be separated therefrom.

When the device according to the present application having the above-described structure is used, the HAT procedure may be easily performed even by a single operator.

For example, an operator adjusts the position of the housing 100 so that the slot S is placed on the scalp laceration site, and then couples the knotting member such as a hook-and-loop fastener to the plurality of knot holes 200 to fix the housing 100 to the scalp of a patient. Then, the operator twists a necessary amount of hair around the scalp laceration site, fixes the twisted hair to the hair fixer 300, and applies skin glue for increasing a fixing strength onto the site of the hair fixer 300 where the hair around the scalp laceration site is fixed. In this way, the HAT procedure may be easily performed by a single operator.

In one example, the hair fixer 300 may include: a mounting portion 310 fitted and coupled to the mounting groove 111 of the housing 100 and having a protruding portion 311 protruding past the frame; and a fixing plate 320 coupled to or decoupled (or separated) from the mounting portion 310 and having an insertion groove 321 into which at least a partial area of the protruding portion 311 is inserted in a state in which the fixing plate 320 is coupled to the mounting portion 310. The protruding portion 311 may be formed to protrude toward the other surface of the frame 110.

In one example, in a state in which the hair around the scalp laceration site is placed on the protruding portion 311, when the mounting portion 310 and the fixing plate 320 are coupled, the hair may be fitted and fixed between the protruding portion 311 and the insertion groove 321. When the mounting portion 310 and the fixing plate 320 are coupled, at least a partial area of the protruding portion 311 is inserted into the insertion groove 321. Here, a slight gap is formed therebetween, and the hair around the scalp laceration site may be fitted to the gap and fixed.

The hair fixer 300 may include: a hinge portion 330 configured to rotatably connect one end of the fixing plate 320 and one end of the mounting portion 310; and a locking portion 400 configured to lock or unlock the other end of the mounting portion 310 and the other end of the fixing plate 320 to or from each other in the state in which the mounting portion 310 and the fixing plate 320 are coupled. The hinge portion 330 rotatably connects the one end of the fixing plate 320 and the one end of the mounting portion 310 for the other ends of the mounting portion 310 and the fixing plate 320 to be rotatable at a predetermined angle. Referring to FIG. 3, in a state in which the hair around the scalp laceration site is placed on the protruding portion 311, the operator may rotate the other end of the fixing plate 320 toward the mounting portion 310 to couple the fixing plate 320 and the mounting portion 310 and then use the locking portion 400 to lock coupling between the mounting portion 310 and the fixing plate 320, thus preventing the mounting portion 310 or the fixing plate 320 from being decoupled due to occurrence of unintentional external impact during the HAT procedure.

As another example, the hinge portion 330 may elastically connect the one end of the fixing plate 320 and the one end of the mounting portion 310 so that, when the other end of the mounting portion 310 and the other end of the fixing plate 320 are unlocked from each other, the fixing plate 320 returns to its original state and reaches a decoupled state in which the fixing plate 320 is spaced from the mounting portion 310 with a predetermined angle therebetween. For example, the hinge portion 330 may be a clip made of an elastic material and connect the other end of the mounting portion 310 and the other end of the fixing plate 320. After the HAT procedure is completed, the operator may unlock the locking portion so that the fixing plate 320 returns to its original state and the fixed hair around the scalp laceration site is released.

In one example, the locking portion 400 may include: a catching protrusion 410 provided at the other end of the mounting portion 310; and a catching step or catching groove 420 provided at the other end of the fixing plate 320 and configured to be caught and coupled to the catching protrusion 410.

In one embodiment, the housing 100 may include a slot S size adjuster configured to adjust the size of the slot S. Using the slot S size adjuster, the housing 100 may freely adjust the size of the slot S corresponding to the size of the scalp laceration site.

For example, the slot S size adjuster may be a length adjuster configured to adjust the length of the frame 110. The slot S size adjuster may adjust the size of the slot S by adjusting the length of the frame 110. For example, the size of the slot S may become smaller when the length of the frame 110 is decreased, and the size of the slot S may become larger when the length of the frame 110 is increased.

In another example, the assistive device for closing scalp lacerations according to the present invention may further include a comb 120 mounted on at least a partial area of the housing 100. The comb 120 is used to tidy the patient's hair before or after the HAT procedure and contributes to increasing the patient's satisfaction with the closing procedure.

The one surface of the frame 110 that comes in contact with the scalp may be curved to come in close contact with the patient's scalp. The curved surface contributes to increasing adhesion between the frame 110 and the scalp. For example, the frame 110 may be manufactured using a known flexible material and thus implemented to be bendable.

The present application also relates to an assistive device for scalp suturing according to another embodiment. Description of content overlapping with the above-described content will be omitted below.

The device includes: a housing 100 including a frame 110 formed in a circular or polygonal shape having a slot therein and two mounting grooves 111 formed at the frame 110 and disposed to face each other with the slot disposed therebetween, wherein the slot S is positioned at a scalp laceration site; a plurality of knot holes 200 provided on at least some areas of the housing; and first and second hair fixers 300*a* and 300*b* each of which is detachably mounted on one of the two mounting grooves of the housing 100 and configured to fix hair around the scalp laceration site.

An operator may cross strands of the hair around the scalp laceration site and fix the crossed strands of the hair to the first and second hair fixers 300*a* and 300*b*. Specifically, the operator may fix the hair adjacent to the second hair fixer 300*b* to the first hair fixer 300*a* and fix the hair adjacent to the first hair fixer 300*a* to the second hair fixer 300*b*, and in this way, the HAT procedure may be easily performed even by a single operator.

Other configurations are the same as the configuration of the above-described assistive device for scalp suturing, and thus detailed description thereof will be omitted.

DESCRIPTION OF REFERENCE NUMERALS

100: housing
200: knot hole
300: hair fixer

The invention claimed is:
1. An assistive device for scalp suturing for patients with scalp lacerations, the assistive device comprising:
   a housing including a frame formed in a circular or polygonal shape having a slot therein and two mounting grooves formed at the frame and disposed to face each other with the slot disposed therebetween, wherein the slot is positioned at a scalp laceration site;
   a plurality of knot holes provided on at least some areas of an outer side of the housing; and
   first and second hair fixers each of which is detachably mounted on one of the two mounting grooves of the housing and configured to fix hair around the scalp laceration site,
   wherein the first and second hair fixers each include:
   a mounting portion fitted and coupled to the mounting groove of the housing and having a protruding portion protruding past the frame; and a fixing plate coupled to or decoupled from the mounting portion and having an insertion groove into which at least a partial area of the protruding portion is inserted in a state in which the fixing plate is coupled to the mounting portion,
   wherein, in a state in which the hair around the scalp laceration site is placed on the protruding portion, when the mounting portion and the fixing plate are coupled, the hair is fitted and fixed between the protruding portion and the insertion groove,
   wherein one surface of the frame that comes in contact with the scalp is curved to come in close contact with the scalp.
2. The assistive device of claim 1, wherein the first and second hair fixers each include:
   a hinge portion configured to rotatably connect one end of the fixing plate and one end of the mounting portion; and
   a locking portion configured to lock or unlock an other end of the mounting portion and an other end of the fixing plate to or from each other in the state in which the mounting portion and the fixing plate are coupled.
3. The assistive device of claim 2, wherein the hinge portion elastically connects the one end of the fixing plate and the one end of the mounting portion so that, when the other end of the mounting portion and the other end of the fixing plate are unlocked from each other, the fixing plate returns to its original state and reaches a decoupled state in which the fixing plate is spaced from the mounting portion with a predetermined angle therebetween.
4. The assistive device of claim 2, wherein the locking portion includes:
   a catching protrusion provided at the other end of the mounting portion; and
   a catching step or catching groove provided at the other end of the fixing plate and configured to be caught and coupled to the catching protrusion.
5. The assistive device of claim 1, wherein the housing includes a slot size adjuster configured to adjust a size of the slot.
6. The assistive device of claim 5, wherein the slot size adjuster includes a length adjuster configured to adjust a length of the frame.
7. The assistive device of claim 1, further comprising a comb mounted on at least a partial area of the housing.

* * * * *